US008900116B2

(12) United States Patent
Hanuka et al.

(10) Patent No.: US 8,900,116 B2
(45) Date of Patent: Dec. 2, 2014

(54) INFLATABLE STOMAL IMPLANT

(75) Inventors: David Hanuka, Ramat-Yishai (IL);
Shay Greenberg, Herzlia (IL); Ron Greenberg, Herzlia (IL)

(73) Assignee: Stimatix GI Ltd., Misgav Business Park (IL)

( * ) Notice: Subject to any disclaimer, the term of this patent is extended or adjusted under 35 U.S.C. 154(b) by 320 days.

(21) Appl. No.: 12/835,838

(22) Filed: Jul. 14, 2010

(65) Prior Publication Data

US 2011/0015475 A1    Jan. 20, 2011

Related U.S. Application Data

(60) Provisional application No. 61/225,546, filed on Jul. 14, 2009.

(51) Int. Cl.
*A61F 2/02* (2006.01)
*A61F 2/04* (2013.01)
*A61F 5/445* (2006.01)

(52) U.S. Cl.
CPC . *A61F 2/04* (2013.01); *A61F 5/445* (2013.01);
*A61F 2002/045* (2013.01); *A61F 2005/4455* (2013.01); *A61F 2250/0003* (2013.01)
USPC .............................. 600/32; 600/31

(58) Field of Classification Search
CPC ........... A61F 2/04; A61F 5/445; A61F 5/441; A61F 5/4407; A61F 2002/045; A61F 2250/0003; A61F 2005/4455
USPC ........... 600/29, 30, 32, 37; 604/332; 606/151; 623/23.64–23.68
See application file for complete search history.

(56) References Cited

U.S. PATENT DOCUMENTS

| | | | |
|---|---|---|---|
| 2,243,529 | A | 5/1941 | Grossman et al. |
| 2,341,984 | A | 2/1944 | Graves |
| 2,510,766 | A | 6/1950 | Surface |
| 2,544,579 | A | 3/1951 | Ardner |
| 2,639,710 | A | 5/1953 | Fazio |
| 2,667,167 | A | 1/1954 | Raiche |
| 2,971,510 | A | 2/1961 | Berger |

(Continued)

FOREIGN PATENT DOCUMENTS

| | | |
|---|---|---|
| CN | 1694661 | 11/2005 |
| EP | 2027835 | 2/2009 |

(Continued)

OTHER PUBLICATIONS

Communication Relating to the Results of the Partial International Search Dated Nov. 17, 2010 From the International Searching Authority Re. Application No. PCT/IL2010/000565.

(Continued)

*Primary Examiner* — Jacqueline Cheng
*Assistant Examiner* — Kaylee Wilson

(57) ABSTRACT

A stomal implant comprising a longitudinal portion configured to envelop at least a section of the bowel or ileal conduit, said longitudinal portion comprising: a proximal end for positioning at a stomal opening; a distal end for positioning within an abdomen; and a reversibly pressure-exerting device providing an ascending pressure gradient from the distal end to the proximal end, such that pressure exerted at the proximal end provides complete closure of the bowel or urethra.

21 Claims, 11 Drawing Sheets

(56) References Cited

U.S. PATENT DOCUMENTS

| | | | |
|---|---|---|---|
| 3,398,744 A | 8/1968 | Hooper | |
| 3,447,533 A | 6/1969 | Spicer | |
| 3,718,141 A | 2/1973 | Goetz | |
| 3,976,076 A | 8/1976 | Beach | |
| 4,030,500 A | 6/1977 | Ronnquist | |
| 4,121,589 A | 10/1978 | McDonnell | |
| 4,170,231 A | 10/1979 | Collins | |
| 4,183,357 A | 1/1980 | Bentley et al. | |
| 4,209,010 A | 6/1980 | Ward et al. | |
| 4,210,131 A | 7/1980 | Perlin | |
| 4,232,672 A | 11/1980 | Steer et al. | |
| 4,265,244 A | 5/1981 | Hill | |
| 4,338,937 A | 7/1982 | Lerman | |
| 4,344,434 A | 8/1982 | Robertson | |
| 4,351,322 A | 9/1982 | Prager | |
| 4,381,765 A | 5/1983 | Burton | |
| 4,399,809 A * | 8/1983 | Baro et al. | 600/31 |
| 4,462,510 A | 7/1984 | Steer et al. | |
| 4,534,761 A | 8/1985 | Raible | |
| 4,634,421 A | 1/1987 | Hegemann | |
| 4,662,890 A | 5/1987 | Burton et al. | |
| 4,721,508 A | 1/1988 | Burton | |
| 4,786,283 A | 11/1988 | Andersson | |
| 4,804,375 A | 2/1989 | Robertson | |
| 4,810,250 A | 3/1989 | Ellenberg et al. | |
| 4,854,316 A * | 8/1989 | Davis | 606/153 |
| 4,863,447 A | 9/1989 | Smith | |
| 4,941,869 A | 7/1990 | D'Amico | |
| 4,950,223 A | 8/1990 | Silvanov | |
| 4,981,465 A | 1/1991 | Ballan et al. | |
| 5,004,464 A | 4/1991 | Leise, Jr. | |
| 5,026,360 A | 6/1991 | Johnson et al. | |
| 5,045,052 A | 9/1991 | Sans | |
| 5,108,430 A | 4/1992 | Ravo | |
| 5,125,916 A | 6/1992 | Panebianco et al. | |
| 5,135,519 A | 8/1992 | Helmer | |
| 5,163,897 A * | 11/1992 | Persky | 600/31 |
| 5,163,930 A | 11/1992 | Blum | |
| 5,261,898 A | 11/1993 | Polin et al. | |
| 5,269,774 A * | 12/1993 | Gray | 604/343 |
| 5,372,594 A | 12/1994 | Colacello et al. | |
| 5,401,264 A | 3/1995 | Leise, Jr. | |
| 5,501,678 A | 3/1996 | Olsen | |
| 5,549,588 A | 8/1996 | Johnson | |
| 5,569,216 A | 10/1996 | Kim | |
| 5,658,266 A | 8/1997 | Colacello et al. | |
| 5,683,372 A | 11/1997 | Colacello et al. | |
| 5,771,590 A | 6/1998 | Colacello et al. | |
| 5,785,677 A | 7/1998 | Auweiler | |
| 5,947,942 A | 9/1999 | Galjour | |
| 6,033,390 A * | 3/2000 | von Dyck | 604/332 |
| 6,050,982 A | 4/2000 | Wheeler | |
| 6,329,465 B1 | 12/2001 | Takahashi et al. | |
| 6,350,255 B1 | 2/2002 | Von Dyck | |
| 6,357,445 B1 | 3/2002 | Shaw | |
| 6,481,589 B2 | 11/2002 | Blomdahl et al. | |
| 6,485,476 B1 | 11/2002 | Von Dyck et al. | |
| 6,595,971 B1 | 7/2003 | Von Dyck et al. | |
| 6,659,988 B1 * | 12/2003 | Steer et al. | 604/333 |
| 6,689,111 B2 | 2/2004 | Mulhauser et al. | |
| 6,695,825 B2 | 2/2004 | Castles | |
| 6,723,079 B2 | 4/2004 | Cline | |
| 6,963,772 B2 | 11/2005 | Bloom et al. | |
| 7,001,367 B2 | 2/2006 | Arkinstall | |
| 7,083,569 B2 | 8/2006 | Boulanger et al. | |
| 7,087,041 B2 | 8/2006 | Von Dyck et al. | |
| 7,250,040 B2 | 7/2007 | Andersen | |
| 7,314,443 B2 | 1/2008 | Jordan et al. | |
| 7,582,072 B2 | 9/2009 | McMichael | |
| 7,670,289 B1 | 3/2010 | McCall | |
| 7,857,796 B2 | 12/2010 | Cline et al. | |
| 8,070,737 B2 | 12/2011 | Cline et al. | |
| 8,092,437 B2 | 1/2012 | Cline | |
| 8,100,875 B2 | 1/2012 | Cline et al. | |
| 8,142,406 B2 | 3/2012 | Blum | |
| 8,388,586 B2 | 3/2013 | Weig | |
| 8,460,259 B2 | 6/2013 | Tsai | |
| 2003/0150050 A1 | 8/2003 | Tanaka et al. | |
| 2003/0199783 A1 | 10/2003 | Bloom et al. | |
| 2003/0220621 A1 | 11/2003 | Arkinstall | |
| 2004/0029467 A1 | 2/2004 | Lacroix | |
| 2004/0073179 A1 | 4/2004 | Andersen | |
| 2004/0122527 A1 * | 6/2004 | Imran | 623/23.67 |
| 2004/0167376 A1 * | 8/2004 | Peters et al. | 600/18 |
| 2004/0171999 A1 | 9/2004 | Andersen et al. | |
| 2004/0181197 A1 | 9/2004 | Cline | |
| 2005/0027159 A1 * | 2/2005 | Feng et al. | 600/30 |
| 2005/0054996 A1 | 3/2005 | Gregory | |
| 2005/0065488 A1 * | 3/2005 | Elliott | 604/361 |
| 2005/0104457 A1 | 5/2005 | Jordan et al. | |
| 2006/0048283 A1 | 3/2006 | Sorensen | |
| 2006/0206069 A1 | 9/2006 | Cline | |
| 2006/0229596 A1 * | 10/2006 | Weiser et al. | 606/37 |
| 2007/0049878 A1 | 3/2007 | Kim et al. | |
| 2007/0142780 A1 | 6/2007 | Van Lue | |
| 2007/0219532 A1 | 9/2007 | Karpowicz et al. | |
| 2007/0276346 A1 | 11/2007 | Poulsen et al. | |
| 2008/0033380 A1 | 2/2008 | Andersen | |
| 2008/0091154 A1 | 4/2008 | Botten | |
| 2008/0108862 A1 | 5/2008 | Jordan et al. | |
| 2008/0135044 A1 | 6/2008 | Freitag et al. | |
| 2008/0275410 A1 | 11/2008 | Burt | |
| 2009/0043151 A1 | 2/2009 | Gobel | |
| 2009/0216206 A1 | 8/2009 | Nishtala et al. | |
| 2009/0247969 A1 | 10/2009 | Nishtala et al. | |
| 2010/0069859 A1 | 3/2010 | Weig | |
| 2010/0174253 A1 | 7/2010 | Cline et al. | |
| 2011/0015475 A1 | 1/2011 | Hanuka et al. | |
| 2011/0040231 A1 | 2/2011 | Gregory | |
| 2011/0106032 A1 | 5/2011 | Kratky | |
| 2012/0136324 A1 | 5/2012 | Hanuka et al. | |
| 2013/0060212 A1 | 3/2013 | Hanuka et al. | |
| 2013/0060213 A1 | 3/2013 | Hanuka et al. | |
| 2013/0079736 A1 | 3/2013 | Hanuka et al. | |
| 2013/0079737 A1 | 3/2013 | Hanuka et al. | |
| 2013/0079738 A1 | 3/2013 | Hanuka et al. | |
| 2013/0116642 A1 | 5/2013 | Hanuka et al. | |
| 2013/0304008 A1 | 11/2013 | Hanuka et al. | |

FOREIGN PATENT DOCUMENTS

| | | | |
|---|---|---|---|
| FR | 2870112 | 11/2005 | |
| GB | 2094153 A * | 9/1982 | A61F 5/44 |
| JP | 2006-314479 | 11/2006 | |
| JP | 2008-507308 | 3/2008 | |
| WO | WO 87/03192 | 6/1987 | |
| WO | WO 90/07311 | 7/1990 | |
| WO | WO 96/32904 | 10/1996 | |
| WO | WO 99/43277 | 9/1999 | |
| WO | WO 01/49224 | 7/2001 | |
| WO | WO 02/058603 | 8/2002 | |
| WO | WO 03/065945 | 8/2003 | |
| WO | WO 03/071997 | 9/2003 | |
| WO | WO 2006/010556 | 2/2006 | |
| WO | WO 2008/048856 | 4/2008 | |
| WO | WO 2008/103789 | 8/2008 | |
| WO | WO 2008/141180 | 11/2008 | |
| WO | WO 2009/083183 | 7/2009 | |
| WO | WO 2009/155537 | 12/2009 | |
| WO | WO 2011/007355 | 1/2011 | |
| WO | WO 2011/138728 | 11/2011 | |
| WO | WO 2011/138731 | 11/2011 | |
| WO | WO 2013/022487 | 2/2013 | |
| WO | WO 2013/168165 | 11/2013 | |

OTHER PUBLICATIONS

International Search Report and the Written Opinion Dated Feb. 28, 2011 From the International Searching Authority Re. Application No. PCT/IL2010/000565.

Notification Concerning Informal Communications With the Applicant Dated May 3, 2012 From the International Searching Authority Re: Application No. PCT/IB2011/051938.

(56) References Cited

OTHER PUBLICATIONS

Notification Concerning Informal Communications With the Applicant Dated May 4, 2012 From the International Searching Authority Re: Application No. PCT/IB2011/051933.
Notification Concerning Informal Communications With the Applicant Dated May 18, 2012 From the International Searching Authority Re: Application No. PCT/IB2011/051932.
Written Opinion Dated Jun. 1, 2012 From the International Preliminary Examining Authority Re. Application No. PCT/IB2011/051938.
Response Dated May 30, 2011 to the Written Opinion of Feb. 28, 2011 From the International Searching Authority Re. Application No. PCT/IL2010/000565.
International Preliminary Report on Patentability Dated Jun. 1, 2012 From the International Preliminary Examining Authority Re. Application No. PCT/IB2011/051933.
International Preliminary Report on Patentability Dated Jun. 5, 2012 From the International Preliminary Examining Authority Re. Application No. PCT/IB2011/051932.
Communication Relating to the Results of the Partial International Search Dated Aug. 12, 2011 From the International Searching Authority Re. Application No. PCT/IB2011/051932.
Communication Relating to the Results of the Partial International Search Dated Aug. 16, 2011 From the International Searching Authority Re. Application No. PCT/IB2011/051933.
International Search Report and the Written Opinion Dated Aug. 18, 2011 From the International Searching Authority Re. Application No. PCT/IB2011/051936.
Communication Relating to the Results of the Partial International Search Dated Aug. 18, 2011 From the International Searching Authority Re: Application No. PCT/IB2011/051938.
International Preliminary Report on Patentability Dated Sep. 6, 2012 From the International Preliminary Examining Authority Re. Application No. PCT/IB2011/051938.
Invitation to Pay Additional Fees Dated Oct. 7, 2011 From the International Preliminary Examining Authority Re. Application No. PCT/IL2010/000565.
International Search Report and the Written Opinion Dated Oct. 19, 2011 From the International Searching Authority Re: Application No. PCT/IB2011/051938.
International Preliminary Report on Patentability Dated Oct. 31, 2011 From the International Preliminary Examining Authority Re. Application No. PCT/IL2010/000565.
International Search Report and the Written Opinion Dated Oct. 14, 2011 From the International Searching Authority Re. Application No. PCT/IB2011/051933.
International Search Report and the Written Opinion Dated Oct. 17, 2011 2011 From the International Searching Authority Re. Application No. PCT/IB2011/051932.
International Preliminary Report on Patentability Dated Nov. 15, 2012 From the International Bureau of WIPO Re. Application No. PCT/IB2011/051936.
Official Action Dated May 9, 2013 From the US Patent and Trademark Office Re. U.S. Appl. No. 13/666,461.
Official Action Dated Jul. 10, 2013 From the US Patent and Trademark Office Re. U.S. Appl. No. 13/680,169.
Official Action Dated Jul. 11, 2013 From the US Patent and Trademark Office Re. U.S. Appl. No. 13/680,161.
Applicant-Initiated Interview Summary Dated Jul. 25, 2013 From the US Patent and Trademark Office Re. U.S. Appl. No. 13/680,161.
Communication Pursuant to Article 94(3) EPC Dated Feb. 11, 2013 From the European Patent Office Re. Application No. 10747082.5.
Official Action Dated Jul. 1, 2013 From the US Patent and Trademark Office Re. U.S. Appl. No. 13/384,343.
Official Action Dated Mar. 25, 2013 From the US Patent and Trademark Office Re. U.S. Appl. No. 13/666,178.
Official Action Dated Mar. 5, 2013 From the US Patent and Trademark Office Re. U.S. Appl. No. 13/666,513.
Translation of Notification of Office Action Dated Jul. 30, 2013 From the State Intellectual Property Office of the People's Republic of China Re. Application No. 201080032032.X.
Applicant-Initiated Interview Summary Dated Jul. 26, 2013 From the US Patent and Trademark Office Re. U.S. Appl. No. 13/666,513.
Applicant-Initiated Interview Summary Dated Jul. 26, 2013 From the US Patent and Trademark Office Re. U.S. Appl. No. 13/680,169.
Communication Relating to the Results of the Partial International Search Dated Sep. 16, 2013 From the International Searching Authority Re. Application No. PCT/IL2013/050401.
Official Action Dated Nov. 7, 2013 From the US Patent and Trademark Office Re. U.S. Appl. No. 13/666,178.
Official Action Dated Nov. 7, 2013 From the US Patent and Trademark Office Re. U.S. Appl. No. 13/680,169.
Official Action Dated Nov. 13, 2013 From the US Patent and Trademark Office Re. U.S. Appl. No. 13/666,461.
Official Action Dated Oct. 16, 2013 From the US Patent and Trademark Office Re. U.S. Appl. No. 13/666,244.
Official Action Dated Oct. 16, 2013 From the US Patent and Trademark Office Re. U.S. Appl. No. 13/666,513.
Official Action Dated Oct. 18, 2013 From the US Patent and Trademark Office Re. U.S. Appl. No. 13/384,343.
Advisory Action Before the Filing of An Appeal Brief Dated Mar. 31, 2014 From the US Patent and Trademark Office Re. U.S. Appl. No. 13/384,343.
Communication Under Rule 71(3) EPC Dated May 19, 2014 From the European Patent Office Re. Application No. 10747082.5.
Notification of Office Action Dated May 6, 2014 From The State Intellectual Property Office of the People's Republic of China Re. Application No. 2011800331827 and Its Translation Into English.
Search Report Dated May 6, 2014 From The State Intellectual Property Office of the People's Republic of China Re. Application No. 2011800331827 and Its Translation Into English.
Official Action Dated Jul. 29, 2014 From the US Patent and Trademark Office Re. U.S. Appl. No. 13/666,244.
Applicant-Initiated Interview Summary Dated Apr. 14, 2014 From the US Patent and Trademark Office Re. U.S. Appl. No. 13/384,343.
Notice of Allowance Dated Apr. 29, 2014 From the US Patent and Trademark Office Re. U.S. Appl. No. 13/680,161.
Notification of Office Action Dated Apr. 18, 2014 From the State Intellectual Property Office of the People's Republic of China Re. Application No. 201080032032.X and Its Translation Into English.
Search Report Dated Apr. 18, 2014 From the State Intellectual Property Office of the People's Republic of China Re. Application No. 201080032032.X and Its Translation Into English.
Notice of Allowance Dated May 8, 2014 From the US Patent and Trademark Office Re. U.S. Appl. No. 13/666,461.
Notice of Reason for Rejection Dated Apr. 15, 2014 From the Japanese Patent Office Re. Application No. 2012-520149 and Its Translation Into English.
Applicant-Initiated Interview Summary Dated Dec. 13, 2013 From the US Patent and Trademark Office Re. U.S. Appl. No. 13/666,244.
Applicant-Initiated Interview Summary Dated Dec. 13, 2013 From the US Patent and Trademark Office Re. U.S. Appl. No. 13/666,513.
Applicant-Initiated Interview Summary Dated Jan. 27, 2014 From the US Patent and Trademark Office Re. U.S. Appl. No. 13/384,343.
Communication Pursuant to Article 94(3) EPC Dated Dec. 17, 2013 From the European Patent Office Re. Application No. 11723672.9.
Communication Pursuant to Article 94(3) EPC Dated Dec. 19, 2013 From the European Patent Office Re. Application No. 11723674.5.
Communication Pursuant to Article 94(3) EPC Dated Dec. 19, 2013 From the European Patent Office Re. Application No. 11724783.3.
International Search Report and the Written Opinion Dated Dec. 20, 2013 From the International Searching Authority Re. Application No. PCT/IL2013/050401.
Official Action Dated Jan. 14, 2014 From the US Patent and Trademark Office Re. U.S. Appl. No. 13/680,161.
Summons to Attend Oral Proceedings Pursuant to Rule 115(1) EPC Dated Nov. 22, 2013 From the European Patent Office Re. Application No. 10747082.5.
Notification of Office Action Dated May 27, 2014 From The State Intellectual Property Office of the People's Republic of China Re. Application No. 201180033162.X.
Official Action Dated Jun. 26, 2014 From the US Patent and Trademark Office Re. U.S. Appl. No. 13/384,343.
Communication Relating to the Results of the Partial International Search Dated Sep. 16, 2014 From the International Searching Authority Re. Application No. PCT/IL2014/050416.
Communication Relating to the Results of the Partial International Search Dated Sep. 16, 2014 From the International Searching Authority Re. Application No. PCT/IL2014/050417.

* cited by examiner

-Configuration #1-

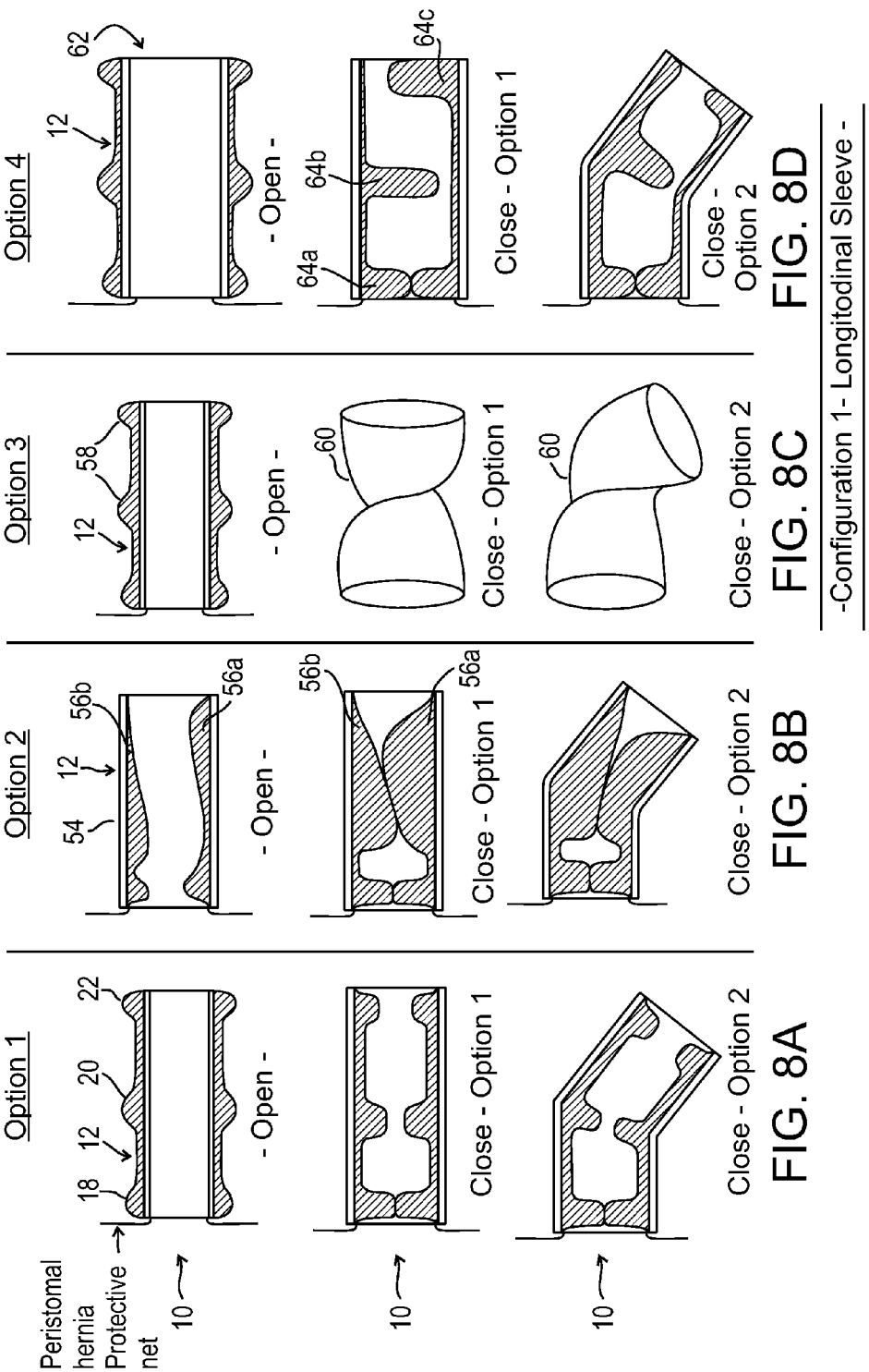

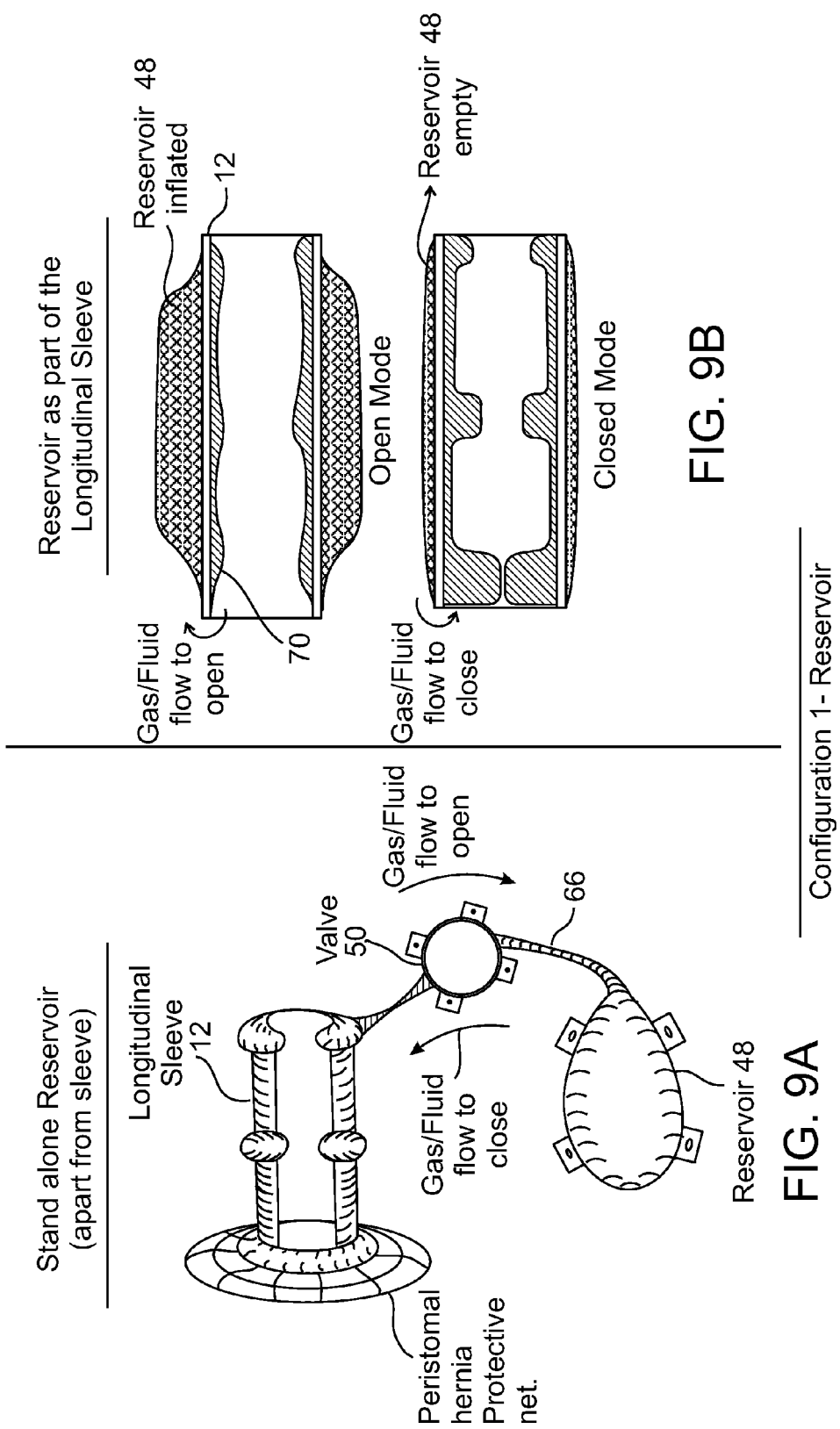

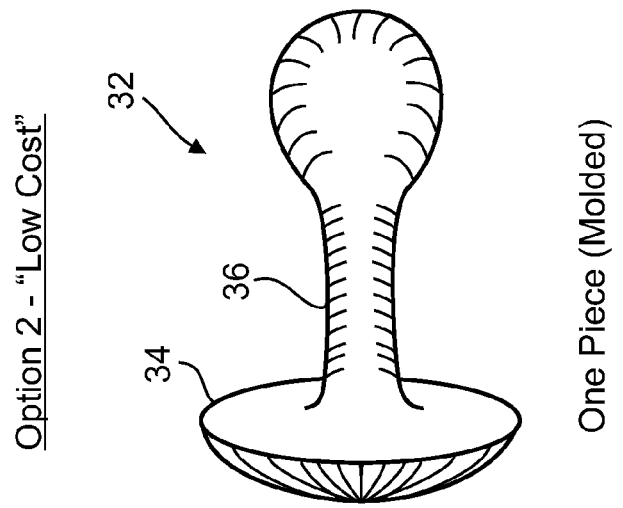
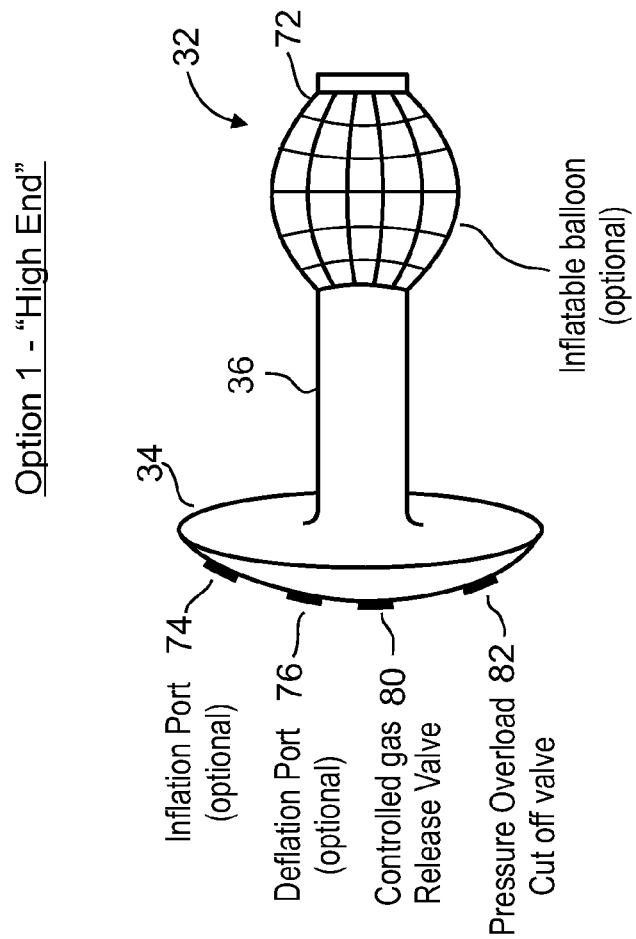
- Configuration 1 - External Closure -

INFLATABLE STOMAL IMPLANT

RELATED APPLICATION

This application claims the benefit of priority under 35 USC 119(e) of U.S. Provisional Patent Application No. 61/225,546 filed Jul. 14, 2009, the contents of which are incorporated herein by reference in their entirety.

FIELD OF THE INVENTION

The present invention relates to the field of prosthetic implants, and more particularly to an inflatable implant for use following Ostomy cases such as Colostomy, Ileostomy or Urostomy, and fecal incontinence.

BACKGROUND OF THE INVENTION

An Ostomy is a surgically created opening in the body for the discharge of body wastes. A stoma is the actual end of the large or small intestine or ureter that can be seen protruding through the abdominal wall. The most common specific types of ostomies are colostomy, ileostomy and urostomy.

A colostomy is a surgically created opening of the colon (large intestine) which results in a stoma. A colostomy is created when a portion of the colon or the rectum is removed and the remaining colon is brought to the abdominal wall.

An ileostomy is a surgically created opening in the small intestine, usually at the end of the ileum. The intestine is brought through the abdominal wall to form a stoma.

A urostomy is a surgical procedure which diverts urine away from a diseased or defective bladder. The ileal or cecal conduit procedures are the most common urostomies. Either a section at the end of the small bowel (ileum) or at the beginning of the large intestine (cecum) is surgically removed and relocated as a conduit for urine to pass from the kidneys to the outside of the body through a stoma. It may include removal of the diseased bladder.

After a colostomy or ileostomy, feces leave the patient's body through an opening in the abdominal wall. External and internal views of stoma and bowel resection are illustrated in FIG. 1A.

After urostomy urine leave the patient's body through an opening in the abdominal wall. An example of a Urostomy is shown in FIG. 1B.

Stoma may be required, for example, following surgical removal of a section of the colon or the small bowel, such that it is no longer possible for the intestinal content to pass out via the anus (e.g. due to colon cancer, diverticulitis, trauma, inflammatory bowel disease, etc.) or following an operation on a section of the bowel which then needs to be rested until it heals. In the latter example, the stoma is often temporary and is reversed at a later date, once healing is complete.

Following a stoma operation, an artificial method of controlled fecal or urine evacuation is required. Such methods may involve non-irrigation systems, involving use of a pouch in which feces or urine is collected (as illustrated in FIG. 2B); or irrigation systems, wherein the bowel is washed out without the use of a pouch.

For irrigation systems, a removable closure, such as a gauze cap, is placed over the stoma, and irrigation is scheduled for specific times. To irrigate, a catheter is placed inside the stoma, and flushed with water, which allows the feces to come out of the body into an irrigation sleeve. Irrigation is generally performed once a day or every other day, though this depends on the person, location of the stoma, their food intake, and their health.

Non-irrigation systems have a number of disadvantages. The pouch is difficult to hide and to keep securely attached, and an odor of feces is frequently detectable. The pouch must generally be emptied or changed several times a day, depending on the frequency of bowel activity. In addition, difficulties in stoma self-care, skin irritation, decreased social relations and sexual problems are commonly reported by patients using the pouch.

WO 96/32904 discloses prosthesis for bowel evacuation control, which is inserted into the intestinal lumen, having a faceplate and a cover to prevent the feces escaping. Such a cover is unlikely to provide a reliable, watertight seal for long term use. Furthermore, it would be expected that build up of gas would occur within the bowel.

There is thus a widely recognized need for, and it would be highly advantageous to have, a stomal implant which is devoid of at least some of the disadvantages of the prior art.

SUMMARY OF THE INVENTION

The present invention provides an inflatable stomal implant for controllable evacuation of body wastes.

The implant preferably comprises a longitudinal portion which encircles the bowel or ileal conduit and holds the waste matter; a removable closure to retain the waste matter within the longitudinal portion; and at least one pressure exerting device which serves to maintain closure of the proximal end of the implant and provide a pressure gradient along the bowel or ileal conduit.

According to one aspect of the present invention, there is provided a stomal implant comprising a longitudinal portion configured to envelop at least a section of a bowel or ileal conduit, the longitudinal portion comprising a proximal end for positioning at a stomal opening, and a distal end for positioning within an abdomen. The implant further comprises at least one pressure-exerting device; and a removable closure for insertion within said proximal end. Insertion of the removable closure within the proximal end and activation of the pressure-exerting device results in a pressure gradient over a section of the bowel or ileal conduit, the pressure gradient providing closure of the bowel or ileal conduit.

The present invention further provides a method for providing fecal continence, the method comprising providing a stomal implant comprising a longitudinal portion configured to envelop at least a section of a bowel or ileal conduit, the longitudinal portion comprising a proximal end for positioning at a stomal opening, a distal end for positioning within an abdomen, at least one pressure-exerting device; and a removable closure for insertion within the proximal end; inserting the stomal implant within said stomal opening; inserting the removable closure within the proximal end; and activating the pressure-exerting device, such that a pressure gradient is provided which retains said removable closure within the proximal end and provides closure of the bowel or ileal conduit.

According to further features in some embodiments of the present invention, the pressure-exerting device comprises a first inflatable device positioned around at least a portion of the circumference of the proximal end.

Optionally, the stomal implant further comprises a second inflatable device positioned around at least a portion of the circumference of the distal end, wherein a pressure exerted on the longitudinal sleeve upon inflation of the first inflatable device is greater than a pressure exerted on the longitudinal portion upon inflation of the second inflatable device, thereby providing a decreasing pressure gradient along the longitudinal sleeve from the proximal end to the distal end.

Further optionally, the longitudinal portion comprises at least a third inflatable device positioned around at least a portion of the circumference of the longitudinal portion, between the first inflatable device and the second inflatable device, wherein a pressure exerted on the longitudinal portion upon inflation of the third inflatable device is greater than a pressure exerted on the longitudinal portion upon inflation of the second inflatable device, and less than a pressure exerted on the longitudinal portion upon inflation of the first inflatable device.

Optionally, the first inflatable device comprises an inflatable ring. Further optionally, the ring extends 360° around said circumference of said longitudinal sleeve.

Optionally, at least one of the second and third inflatable devices comprises an inflatable ring, which further optionally extends 270° around the circumference of the longitudinal portion.

Optionally, the inflatable device is inflated by insertion of a fluid, such as a liquid (for example, saline), a gel, a colloid, a suspension, an emulsion, a gas, or a supercritical fluid, which further optionally is contained within a reservoir prior to inflation of the inflatable device. Such a reservoir may optionally be located intra-abdominally or retroperitoneally, or alternatively, may be positioned on the longitudinal portion. Further optionally, the reservoir may comprise a plurality of separate compartments, wherein each compartment serves as a reservoir for a single inflatable device.

Optionally, the implant further comprises an activator valve in communication with the reservoir, wherein activation of the activator valve forces fluid from the reservoir into at least one of said rings. The activator valve is optionally positioned subcutaneously.

According to some embodiments, the implant further comprises a port, in fluid communication with the reservoir, wherein the port provides control of flow of fluid from the reservoir to at least one ring.

According to some embodiments, the implant is attached to the intra abdominal wall, for example by at least one of a suture, a clip or a staple, or combinations thereof.

Optionally, the implant is constructed from silicon or polyurethane.

The removable closure of the present invention optionally comprises a base located at a proximal end and a protruding section. The base optionally comprises a flattened section having a circumference greater than that of the inflatable first ring in an inflated state. Optionally, the flattened section is configured to adhere to the skin of the outer abdominal wall.

The protruding section of the closure optionally comprise a stem and a bulbous distal end, the bulbous end being sealingly retained within the proximal end of the longitudinal sleeve upon inflation of the first ring. According to some embodiments, the removable closure comprises a reversibly inflatable balloon at a distal end.

Optionally, the implant of the present invention further comprises a protective layer for positioning around said proximal end for prevention of peristomal hernia.

According to some embodiments, the pressure-exerting device comprises a reversibly inflatable balloon fixedly attached to a distal end of the removable closure.

According to some embodiments, the removable closure further comprises at least one of a unidirectional gas valve, an inflation port, a deflation port and a pressure overload cutoff valve. Optionally, the unidirectional gas valve is manually controllable by a user.

The stomal implant is simple and convenient to operate by the stomal patient, and enables the user to remove waste matter and gases at a time and location which is convenient for the user. The implant provides hermetic sealing of the stoma, and thereby enables stoma patients to enjoy an increased quality of life, including participation in activities such as swimming and other physical activities, without the need to rely on scheduled irrigation sessions, or on use of an unaesthetic pouch.

Operation of the inflatable-deflatable stomal implant of the present invention is based on the physiological operation of the anorectal sphincter. The implant of the present invention provides a gradual pressure gradient along the relevant portion of the intestine or ileal conduit, increasing from the distal to the proximal ends, wherein the maximum pressure at the proximal end does not exceed 200 mmHg. Use of such a pressure gradient prevents or reduces the risk of ischaemia, blood vessel occlusion or necrosis associated with the application of pressure at a specific point over an extended time period. Structuring the implant in the form of a longitudinal sleeve that closes a section of the intestine or the ileal conduit significantly reduces the risk of incontinence due to single point failure which may occur with prior art devices that provide closure only at one location. Bending of the longitudinal sleeve when in the closed configuration further reduces the risk of leakage. The sleeve may optionally be connected to any portion of the bowel or ileal conduit of the patient.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Where ranges are given, endpoints are included within the range. Furthermore, it is to be understood that unless otherwise indicated or otherwise evident from the context and understanding of one of ordinary skill in the art, values that are expressed as a range can assume any specific value or subrange within the stated range in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 8A-D shows alternative embodiments of the pressure-exerting device of the implant of the present invention;

FIG. 9A shows an embodiment of the implant of the present invention wherein the reservoir is provided as a separate device from the longitudinal sleeve; FIG. 9B shows an embodiment of the present invention wherein the reservoir is provided as an integral part of the longitudinal sleeve;

FIG. 10A and 10B show alternative embodiments of the external closure of the implant of the present invention.

DESCRIPTION OF THE PREFERRED EMBODIMENTS

Figure 1A:
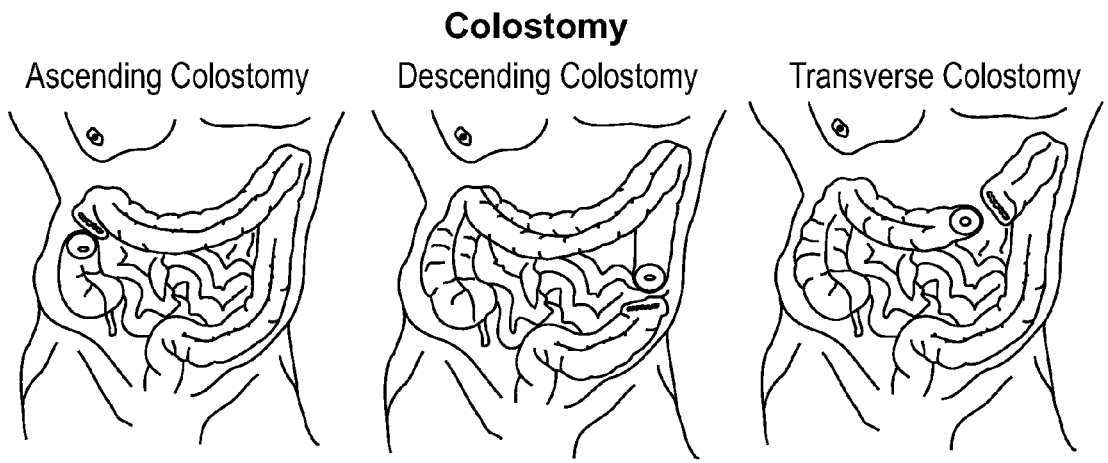
FIG. 1A is an illustration of a bowel resection and colostomy.
Figure 1B:
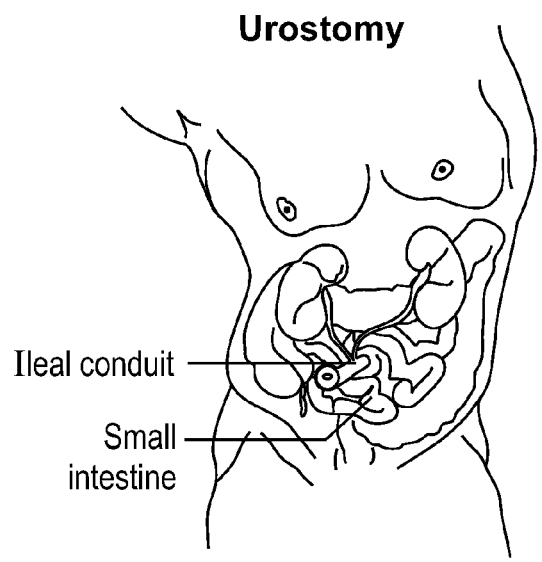
FIG. 1B is an illustration of a urostomy.
Figure 2A:
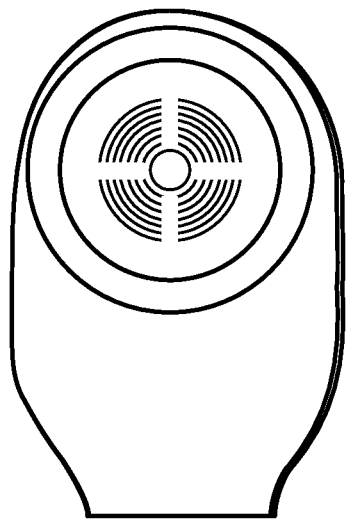
FIG. 2A is an illustration of a prior art colostomy pouch.
Figure 2B:
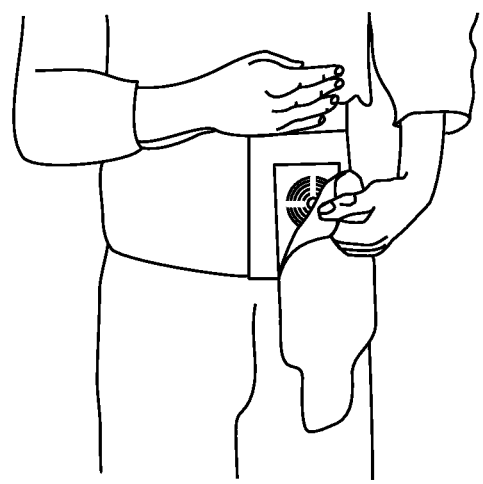
FIG. 2B illustrates placement of the prior art colostomy pouch on the body of a stoma patient.

The present invention provides a stomal implant for controllable faeces or urine evacuation.

According to some embodiments, the implant comprises a longitudinal portion, such as a sleeve configured to envelop at least a section of the bowel or ileal conduit inside the abdominal cavity, around the outer circumference, the implant having a proximal end for positioning at the stomal opening in the inner abdominal wall, a distal end for positioning within the abdomen, and at least one reversibly pressure-exerting device for providing a gradual pressure gradient along the longitudinal sleeve.

Optionally, the implant further comprises a removable closure having at least a portion which is configured so as to be sealingly insertable within the stomal opening to provide a seal, which is preferably a water-tight seal.

Herein the term "proximal" generally refers to the side or end of an elongated medical device that is intended to be closer to the performing medical personnel, and is generally located outside or at the surface of the body of the patient.

Herein the term "distal" generally refers to the side or end of an elongated medical device that is intended to be further from the performing medical personnel.

According to some embodiments, the implant extends into the abdomen from the stomal opening inside the abdominal cavity connected to the inner abdominal wall, encircling at least a section of the bowel or ileal conduit with the proximal end of the implant being positioned at the stomal opening, perpendicular to the abdominal wall, and attached to the intra abdominal wall by any conventional securing device, such as, for example, sutures, clips, staples, or a biocompatible glue (such as an acrylic glue).

According to some embodiments, the implant further comprises at least one, such as for example one, two, three, or more inflatable-deflatable pressure-exerting devices, configured to reversibly exert a gradually increasing pressure gradient along at least a portion of the length of the longitudinal sleeve, from the distal end to the proximal end, wherein the pressure is sufficient to provide full closure of the bowel or ileal conduit. The pressure-exerting device may, for example, comprise a single portion along which the pressure exerted can be varied, or may comprise two or more distinct portions, each exerting a different pressure.

Optionally and preferably, the pressure-exerting devices are positioned on, and at least partially encircling, the outer circumference of the longitudinal sleeve. Further optionally, the pressure-exerting devices may be integral to the longitudinal sleeve.

Optionally and preferably, the pressure gradient exerted ranges from about 0 up to about 200 mm Hg. More preferably, local pressure along a portion of the longitudinal sleeve does not exceed 30-60 mmHg at any specific point, to avoid the blood vessel occlusion. Hence, the maximum pressure reached at a specific point may be, for example, 60 mmHg, 55 mm Hg, 50 mmHg, 45 mmHg, 40 mmg Hg, 35 mmHg, 30 mmHg, or less.

According to some embodiments, the pressure-exerting device comprises a reversibly inflatable or deflatable device, such as, for example, a ring. Optionally, the pressure exerted upon inflation of the pressure-exerting device is adjustable, either by automatic control to a preset level upon activation, or manually by the user.

Inflation of the inflatable device may optionally be achieved by insertion of a fluid, such as saline or similar biocompatible, sterile liquid, a gel, a colloid, a suspension, an emulsion, a gas, or a supercritical fluid.

According to a preferred embodiment, at least a first pressure-exerting device is positioned on the longitudinal sleeve at the proximal end of the intestine or ileal conduit, and a second pressure-exerting device is positioned at the distal end of the longitudinal sleeve, wherein the pressure exerted by the first pressure-exerting device is greater than that exerted by the second pressure-exerting device. The pressure-exerting device is able to mimic the action of the anorectal sphincter, thereby reversibly sealing the stomal opening around the removable closure.

Optionally, the implant further comprises a third pressure-exerting device, located on the longitudinal sleeve between the first and the second pressure-exerting devices, and exerting a pressure which is intermediate between that exerted by the first and the second pressure-exerting devices.

According to an exemplary embodiment of the implant of the present invention, the first pressure-exerting device comprises a full 360° ring. According to some embodiments, the implant further comprises a second inflatable ring, positioned at the distal end of the longitudinal sleeve, which, upon inflation, exerts a pressure on the sleeve which is lower than that exerted by the first ring upon inflation. Optionally, the implant further comprises a third inflatable ring, positioned on the longitudinal sleeve, between the first and the second inflatable rings, which, upon inflation, exerts a pressure intermediate between that of the inflated first and second rings. Optionally and preferably, the second and third rings are partial rings, such as 270° rings, which thereby allow uninterrupted vascular supply from the colon mesentery.

According to some aspects of this embodiment, the rings are constructed from silicon or Polyurethane or similar biocompatible and expandable material.

According to some embodiments of the present invention, the pressure-exerting device may comprise, for example, one or more controllable closures, which may be opened or closed to various degrees, to exert varying degrees of pressure on the longitudinal portion. Alternatively, the pressure-exerting device may comprise a device for providing controlled bending or twisting of the longitudinal portion.

According to some embodiments, the longitudinal sleeve comprises silicon embedded with a mesh. The mesh may be constructed from any flexible, biocompatible material known in the art.

According to some embodiments wherein the pressure-exerting device is reversibly inflatable by use of a fluid, the fluid is contained in a reservoir when the implant is in the deflated state. The reservoir is optionally located intra-abdominally or retroperitoneally, in fluid communication with the pressure-exerting device, further optionally via a valve. Alternatively, the reservoir may be fixed to a surface of the implant, or may be provided as in integral part of the outer portion of the implant. Optionally, the reservoir may comprise a plurality of separate compartments, each compartment serving as a reservoir for a single pressure-exerting device.

According to some embodiments, the reservoir is connected, for example via a tube, to at least one activator valve, which can be activated so as to exert pressure on the reservoir, thereby forcing the fluid from the reservoir into the pressure-exerting device. The valve functions as an activator-deactivator control. For example, according to one non-limiting example, the valve may be activated by pressing once, whereby fluid from the reservoir flows into the pressure-exerting device, causing inflation. By pressing once more, the solution may flow from the pressure-exerting device back into the reservoir, thereby deflating the pressure-exerting device. The flow of fluid between the reservoir and the pressure-exerting device is generated via a pressure gradient.

According to some embodiments, the reservoir is positioned subcutaneously, and is attached to the inner abdominal wall by any method known in the art, such as, for example, suturing, stapling, clipping, or gluing with a biocompatible glue. The location of the reservoir is selected so as to provide convenient access by the user, and the reservoir is preferably positioned against a firm surface, such as a bone. The reservoir may be positioned, for example, against the pelvic bone, the pudendal bone, the breast bone, or the ribcage.

According to some embodiments, the activator valve is positioned subcutaneously, and is attached to the inner abdominal wall by any method known in the art, such as, for example, suturing, stapling, clipping, or gluing with a biocompatible glue. The location of the valve is selected so as to provide convenient access by the user, and the valve is preferably positioned against a firm surface, such as a bone. The valve may be positioned, for example, against the pelvic bone, the pudendal bone, the breast bone, or the ribcage.

According to some embodiments, the valve may optionally be mechanically or electrically operated, such as, for example, a micro pump.

According to some embodiments, the implant further comprises a port, in fluid communication with the reservoir, for example via a tube, to increase or decrease fluid volume, preferably within each separate compartment, in order to provide individual pressure control for the rings in accordance with the anatomy of the individual patient. The port may also be used for refilling of the reservoir in the event that fluid leakage occurs.

Upon inflation, the pressure-exerting devices provide different pressure levels creating a gradual decrement of pressure from the distal end to the proximal end establishing full closure the bowel, such that a pressure gradient is established along the length of the longitudinal sleeve. For example, the second pressure-exerting devices, positioned at the distal end of the longitudinal sleeve may optionally provide a higher pressure than that provided by the third pressure-exerting devices, which is in turn higher than that of the first pressure-exerting device located at the distal end of the longitudinal sleeve. The pressure gradient thereby established mimics physiological bowel pressure, and provides decreasing pressure towards the stomal opening, thus providing closure of the stoma.

Upon deflation of the pressure-exerting devices, no pressure is provided, such that no closure of the stoma is produced, thereby enabling the contents of the implant to be evacuated. Deflation may be achieved, for example, by providing a bidirectional pump, or by operation of a valve which causes a counter-pressure to be exerted on the pressure-exerting device, such that the fluid is forced back into the reservoir. The contents of the implant may be evacuated, for example, by allowing natural peristalsis to cause emptying when the pressure-exerting device is in the deflated mode; by irrigation; or by adjustment of the pressure gradient by controlled opening of the rings, such that the contents are forced outwards.

Optionally and preferably, the implant further comprises a protective layer, such as a net layer, for prevention of peristomal hernia by protection of the abdominal peritoneum.

Figure 3:
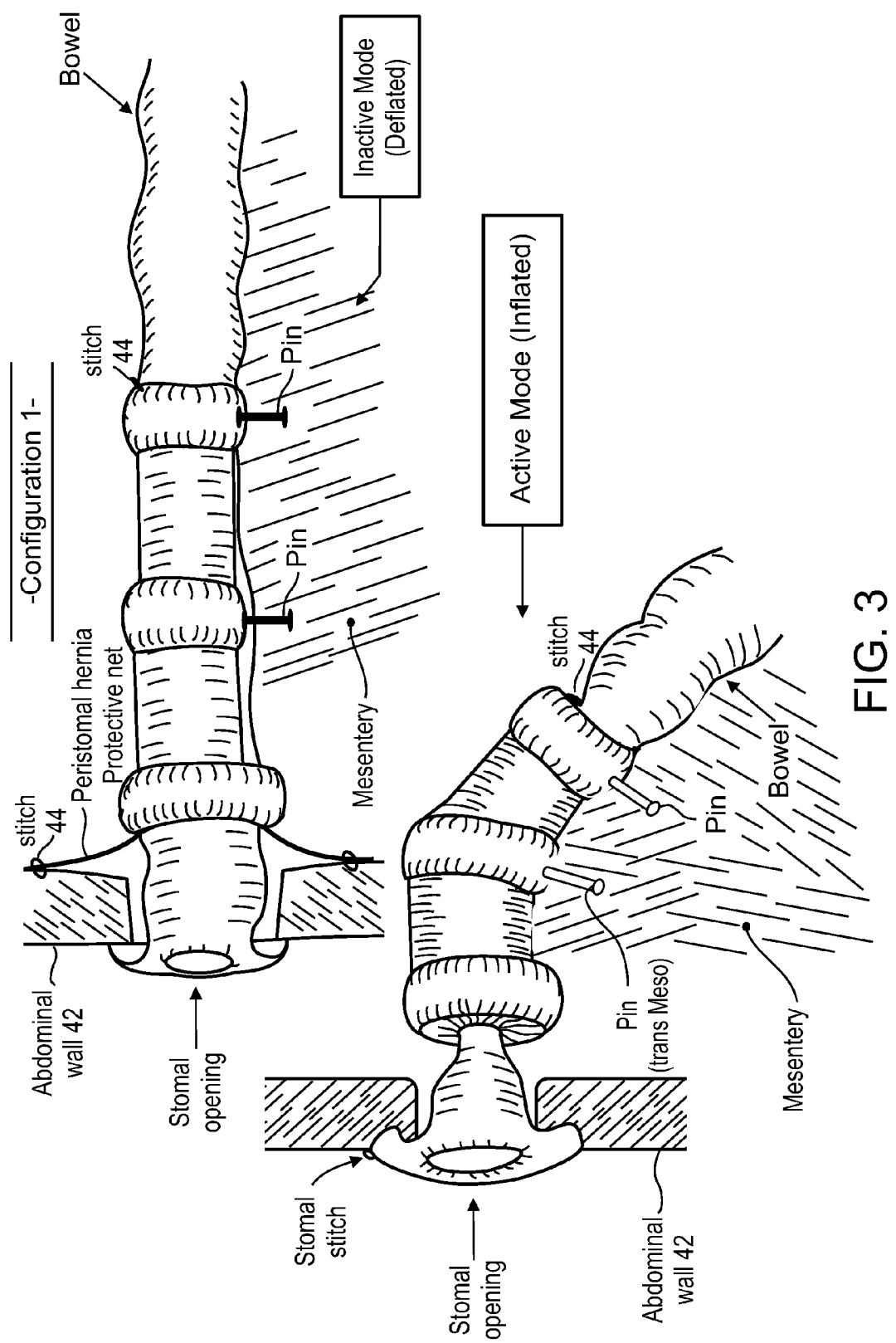
FIG. 3 illustrates the arrangement of the pressure-exerting implant of the present invention with the inflatable portion deflated and inflated.

Optionally and preferably, as shown in FIG. 3, the entire length of the longitudinal sleeve in the deflated state is positioned parallel to the abdominal cavity, whereas in the active state the axis of the second and third pressure-exerting devices is preferably adjusted to an angle of 40-60° to that of the abdominal cavity. This angle may further help in maintaining stomal closure by decreasing the fecal or urinary pressure towards the stomal opening, thus mimicking the physiological angle of the human anal or urinary canal.

According to some embodiments, the closure comprises protruding longitudinal section which is insertable via the proximal end of the implant, and a base section having a circumference greater than that of the outer circumference of the open distal end, and which remains outside the stomal opening. The base may comprise, for example, a flattened portion which can adhere to the outside of the abdominal wall, further sealing the stomal opening and providing an aesthetic covering of the stoma.

The longitudinal section may optionally be provided with a distal end having a circumference greater than that of the longitudinal section, such as, for example, a bulbous end, wherein upon exertion of pressure by the pressure-exerting device on the, the longitudinal section, proximal to the bulbous end, the bulbous end is firmly retained within the proximal end of the implant, forming a seal.

The removable closure may optionally be provided as a one piece molded unit, comprising, for example, the base, the longitudinal section, and the distal end.

Alternatively and also optionally, the closure may be provided with a distal end comprising an inflatable device, such as a balloon. According to such an embodiment, the inflatable device of the distal end may optionally be controllable by inflation and deflation ports located outside the stoma, which may be, for example, positioned on the outer surface of the base section. Inflation and deflation ports may be combined as a single unit control port. Such an embodiment has the advantage of providing a passive sleeve, wherein the extent of the portion implanted within the body is kept to a minimum, and operation of the implant is generally controlled from outside the body.

The closure may be constructed, for example, from silicon. The closure is held in place by the proximal ring and may optionally be covered with an adhesive material.

According to some embodiments, the implant is optionally further provided with a manometer which determines pressure levels within the implant. The manometer may optionally be provided with a device, such as a light or sound device, for visually or audibly alerting the user of the need to evacuate the contents of the implant once a critical pressure is reached.

According to some embodiments, the closure comprises a unidirectional gas valve, which allows gas to exit the bowel, thereby preventing excessive gas accumulation, which may lead to barotrauma of the bowel. Preferably, the valve is configured such that gas does not exit the bowel until a predefined maximum pressure is reached. Once the maximum pressure level is exceeded, gas is released via the valve. Optionally and preferably, the valve may be manually controllable by the user up to the predefined maximum pressure level. The gas valve thereby prevents uncontrolled spontaneous flatulence.

Alternatively, or additionally, the closure may be provided with a valve for prevention of overload, such that automatic dispersion of pressure occurs if pressure exceeds 30-80 mmHg, thereby avoiding the risk of damage to blood vessels, such as ischaemia. The cutoff pressure can also be fine tuned to the desired pressure as needed.

The stomal implant of the present invention may be inserted into the abdomen either during the surgical procedure to create the stoma, or may be inserted at a subsequent time.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As used herein the term "about" refers to ±10%.

Figure 4:
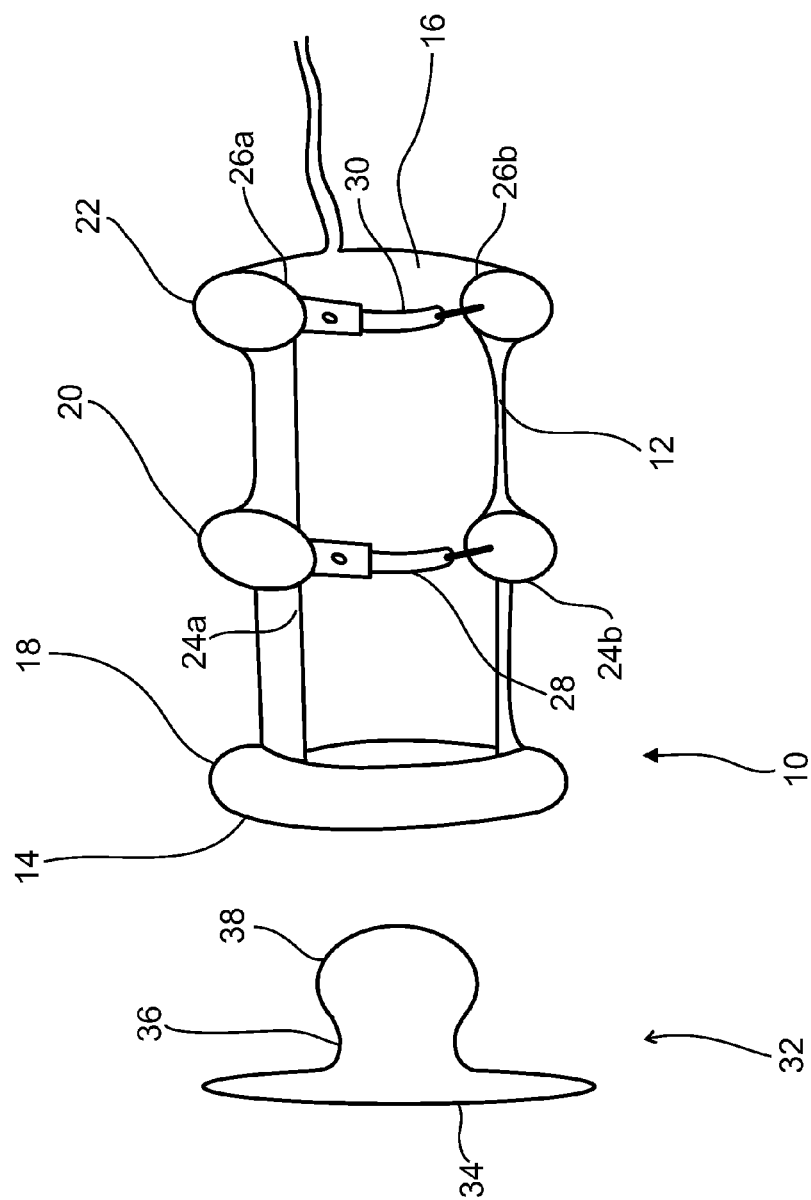
FIG. 4 is a side view of the pressure-exerting implant of the present invention.

According to one embodiment as shown in FIG. 4, the implant 10 of the present invention comprises a longitudinal sleeve 12, having a proximal end 14, and a distal end 16. An integral, inflatable/deflatable ring 18 is provided around end 14, such that when inflatable ring 18 is in a deflated state, proximal end 14 is open, while closure of proximal end 14 is achieved by full inflation of inflatable ring 18. Longitudinal sleeve 12 is configured to be positioned around the external wall of at least a section of the bowel or ileal conduit.

Implant 10 further comprises partial rings 20 and 22, wherein partial ring 22 is positioned around the circumference of proximal end 16 of longitudinal sleeve 12, and partial ring 20 is positioned around a portion of the axis of longitudinal sleeve 12, between ring 18 and partial ring 22. Partial rings 20 and 22 extend approximately 270° around the outer circumference of longitudinal sleeve 12. Open ends 24a, 24b, and 26a, 26b, of partial rings 20 and 22, respectively, are held in position by pins 28 and 30, respectively, which may be constructed, for example, from silicon.

Implant 10 further comprises a removal closure 32, configured for insertion within a section of the colon held within ring 18 of distal end 14, such that when closure 32 is inserted within the colon within ring 18, a water-tight seal is formed at proximal end 14.

Closure 32 comprises a flattened base 34, a stem 36, and a bulbous end 38 positioned on stem 36, such that closure 32 resembles a pacifier in shape.

Inflation and deflation of rings 18, 20, and 22 of implant 10 are optionally controlled manually by the user, providing bowel control in colostomy patients. Alternatively, control can be achieved electrically, for example using an active device such as a pump.

Figure 5:
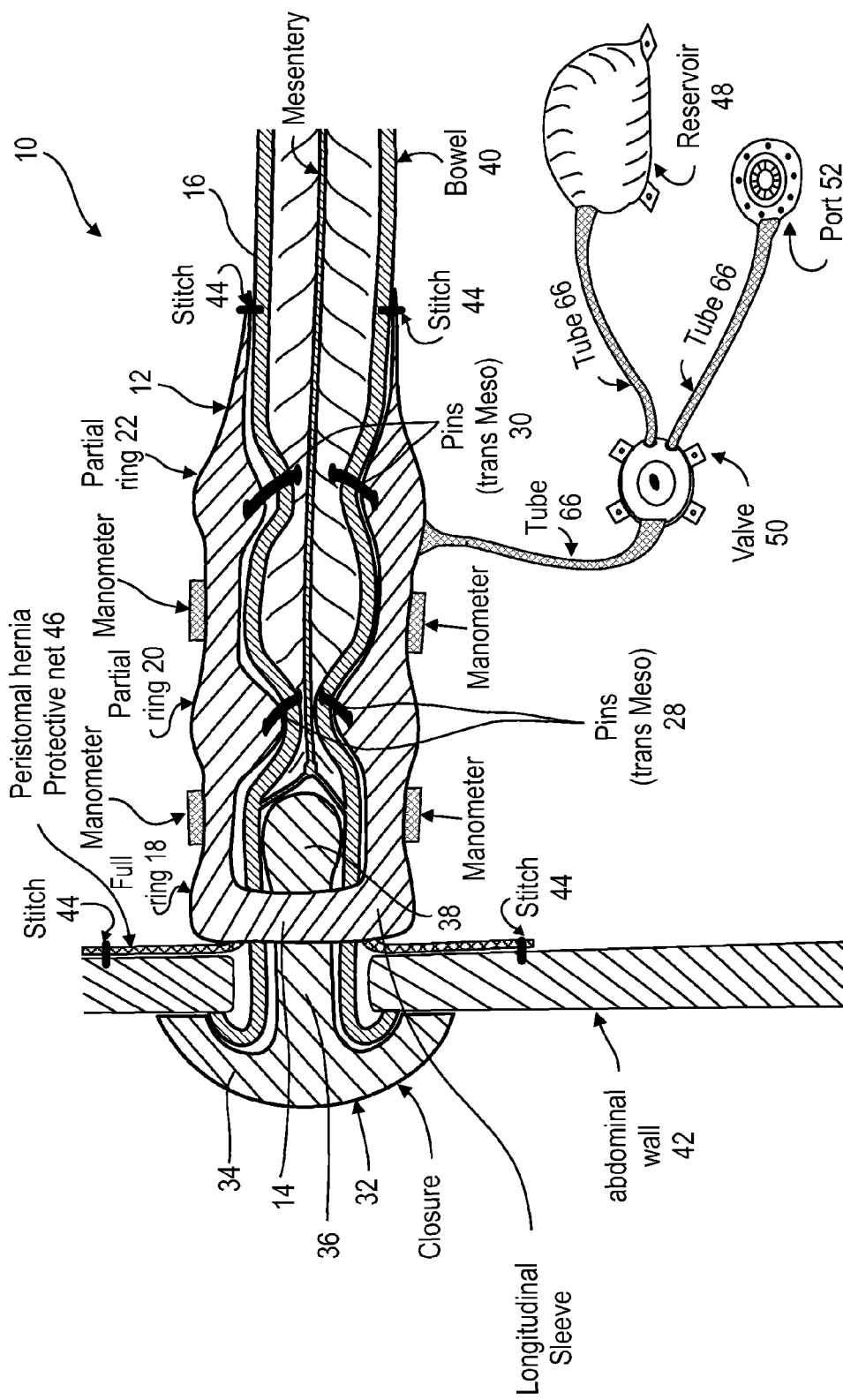
FIG. 5 is a side view of the implant of the present invention, located within the abdomen.

FIG. 5 shows implant 10 positioned within the bowel 40 of a subject. As shown, longitudinal sleeve 12 is positioned within bowel 40, such that proximal end 14 is proximal to abdominal wall 42, and distal end 16 is within the length of bowel 40. Implant 10 may be attached to bowel 40 and/or to abdominal wall 42 by one or more stitches 44, at various locations. Alternatively or additionally, implant 10 may be retained in position by use of one or more staples, and/or clips, and/or by use of biocompatible glue.

Following implantation of implant 10 within bowel 40, removable closure 32 is inserted within proximal end 14, with inflatable rings 18 in the deflated state. Upon inflation of ring 18, closure 32 is firmly gripped by ring 18, such that a water-tight seal is formed at proximal end 14.

Implant 10 optionally further comprises a peristomal hernia protective layer or mesh 46, such as a netting material, positioned around said proximal end 14 for prevention of peristomal hernia.

Implant 10 further comprises reservoir 48 for containing fluid, such as saline. Activator valve 50, positioned at a subcutaneous location which is easily accessible by the user, controls flow of fluid from reservoir 48 to inflatable rings 18, 20, 22 of longitudinal sleeve 12. The volume of fluid flow from reservoir 48 to longitudinal sleeve 12 is further modulated by port 52 via valve 50.

Figure 6:
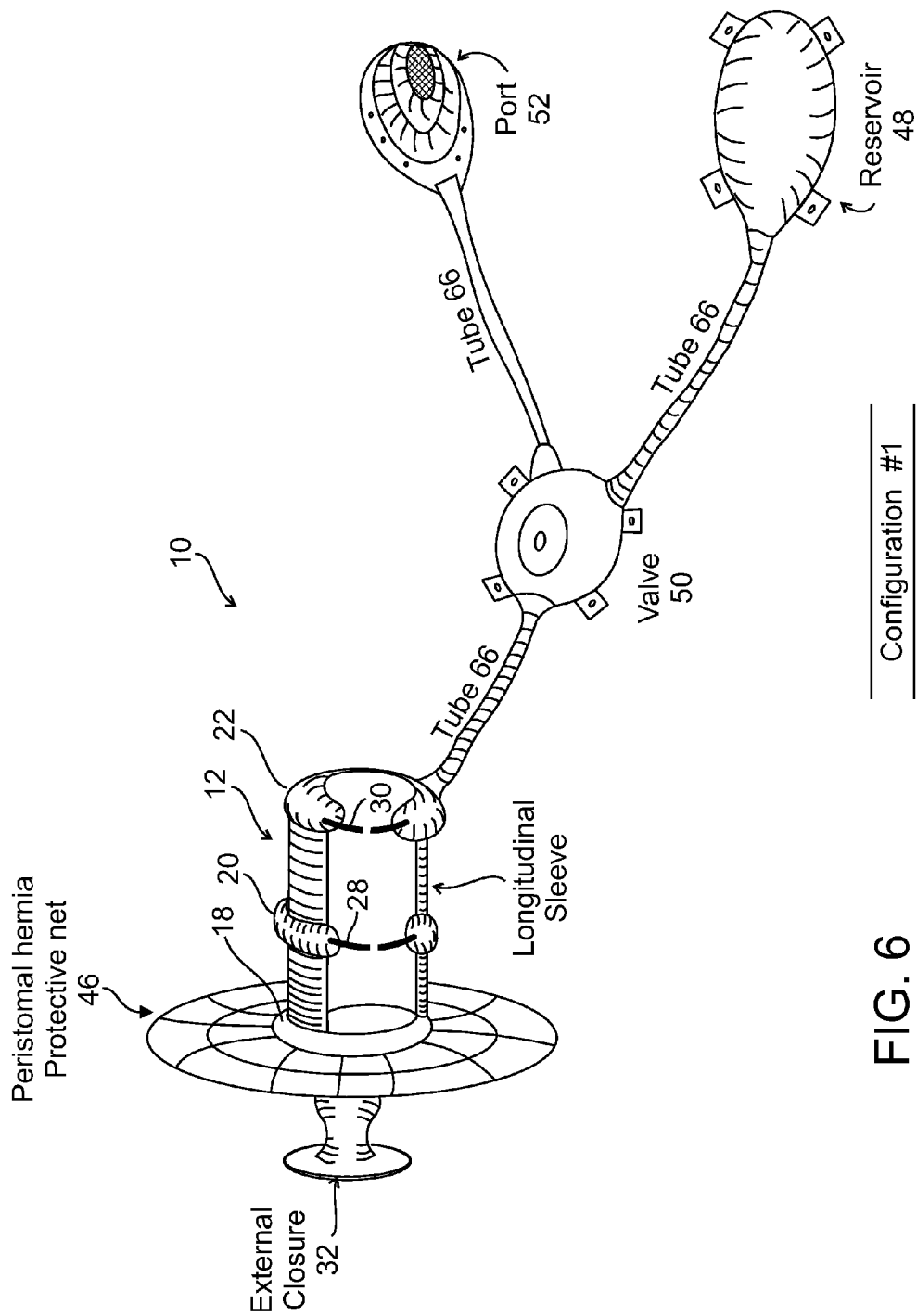
FIG. 6 is a side view of a further embodiment of the implant of the present invention.

FIG. 6 further illustrates implant 10, wherein longitudinal sleeve 12, comprising inflatable ring 18 and partial rings 22 and 24, provided with pins 28 and 30, is in fluid communication with reservoir 48. Flow of fluid from reservoir 48 is controlled by activator valve 50, and fluid volume is controlled by port 52 via valve 50. Protective layer 46 is positioned around said proximal end 14 for prevention of peristomal hernia.

Figure 7:
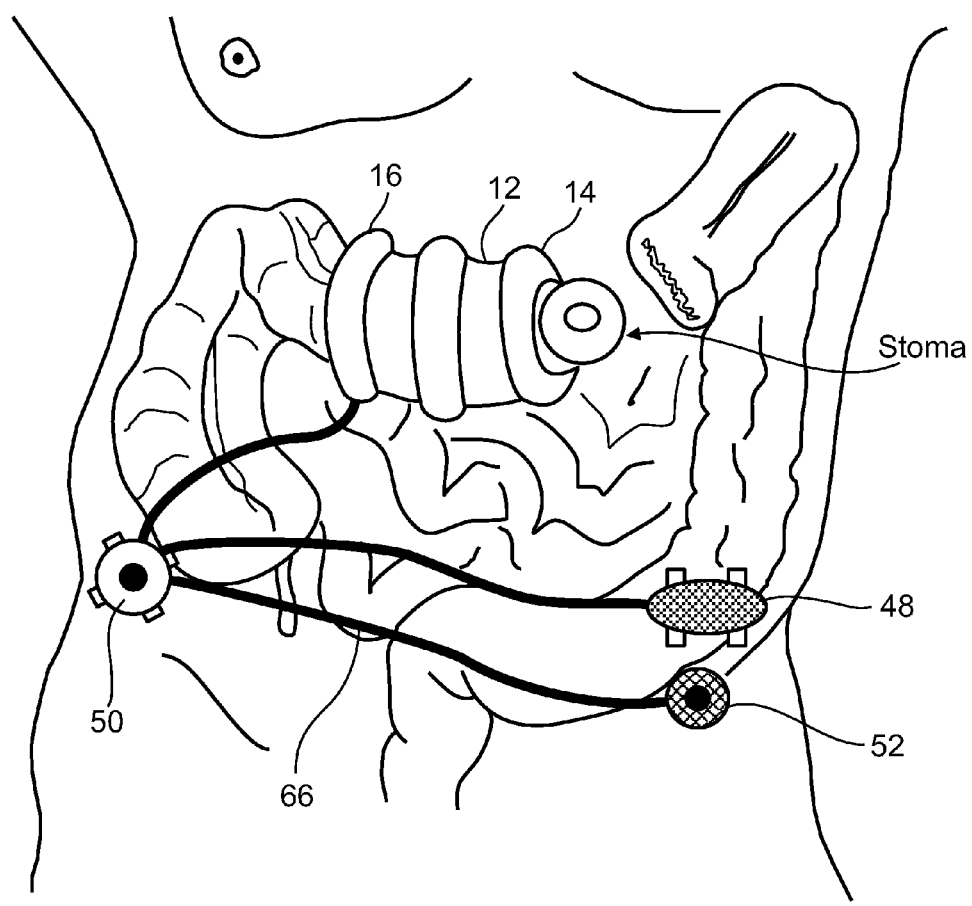
FIG. 7 shows the implant of the present invention within the body of a subject.

FIG. 7 illustrates the implant of the present invention positioned within the body of a patient.

Shown are longitudinal sleeve 12, having proximal end 14 and distal end 16, positioned around a portion of the colon. Longitudinal sleeve 12 is in fluid communication with reservoir 48, and port 52 via tube 66, with flow controlled by valve 50.

FIGS. 8A-8D illustrate optional embodiments of the pressure-exerting device of the implant of the present invention. In each embodiment, when the pressure-exerting device is in the open (inactivated) mode, no pressure is exerted on the longitudinal section of the implant. Pressure is exerted upon activation of the pressure-exerting device. According to some embodiments, at least a portion of the pressure-exerting device remains partially open upon activation, in order to prevent the occurrence of ischemia or necrosis.

FIG. 8A shows implant 10, provided with inflatable ring 18, and partial rings 20 and 22, as described in detail above for FIG. 4. As shown in FIG. 8A, when rings 18, 20 and 22 are in open mode, no pressure is exerted on longitudinal section 12. Upon inflation, pressure is exerted on longitudinal sleeve 12.

FIG. 8B shows pressure-exerting device 54, having at least two shaped segments 56a, 56b, which are brought together upon activation of pressure-exerting device 54. Segments 56a, 56b may have any suitable shape, provided the segments may be adjusted decrease the circumference of device 54, such as by bringing the edges of segments 56a, 56b together, or causing segments 56a, 56b to overlap or wedge.

FIG. 8C shows pressure-exerting device 58, wherein upon activation of device 58, longitudinal sleeve 12 is caused to twist over the longitudinal axis at an angle of 30-60°, or to bend at an angle of 40-60°, thereby providing a closure at a predetermined point 60 on longitudinal sleeve 12.

FIG. 8D shows a further alternative embodiment 62 of the pressure-exerting device of the present invention, comprising elongated, curved portions 64a, 64b, 64c, configured to close around longitudinal sleeve 12 to various extents, to provide varying degrees of pressure.

According to any of the embodiments shown in FIGS. 8A-8D, the axis of the longitudinal portion may be unchanged upon activation of the pressure-exerting device. Alternatively, activation of the pressure-exerting device may cause the axis of the implant to be adjusted to an angle of about 40-60° to that of the abdominal cavity, in order to decrease fecal or urinary pressure towards the stomal opening, thus mimicking the physiological angle of the human anal canal (closed mode 2 for each Figure).

FIGS. 9A and 9B illustrate optional embodiments of the reservoir of the present invention. FIG. 9A shows an embodiment wherein reservoir 48 is in fluid communication with longitudinal portion 12 via tube 66, optionally controllable by valve 50. FIG. 9B illustrates an alternative optional embodiment, wherein reservoir 48 is located on an outer surface of longitudinal portion 12, wherein controlled flow of fluid between reservoir 48 and pressure-exerting device 70 causes activation/deactivation of pressure exerting device 70.

FIGS. 10A and 10B illustrate optional embodiments of the removable closure of the present invention.

FIG. 10A shows closure 32 comprising base 34, stem 36, and distal end 72, which may be inflated after positioning of closure 32 within the implant, thus providing greater ease of insertion of closure 32. Control of inflation of inflatable distal end 72 may optionally be achieved by use of inflation port 74 and deflation port 76, which are located on the outer surface of base 34. Closure 32 optionally further comprises a valve 80 for controlled gas release which may be controlled automatically, or manually by the user; and a safety cut off valve 82 which is automatically activated upon build up of pressure beyond a predetermined safety limit.

Figure 11:
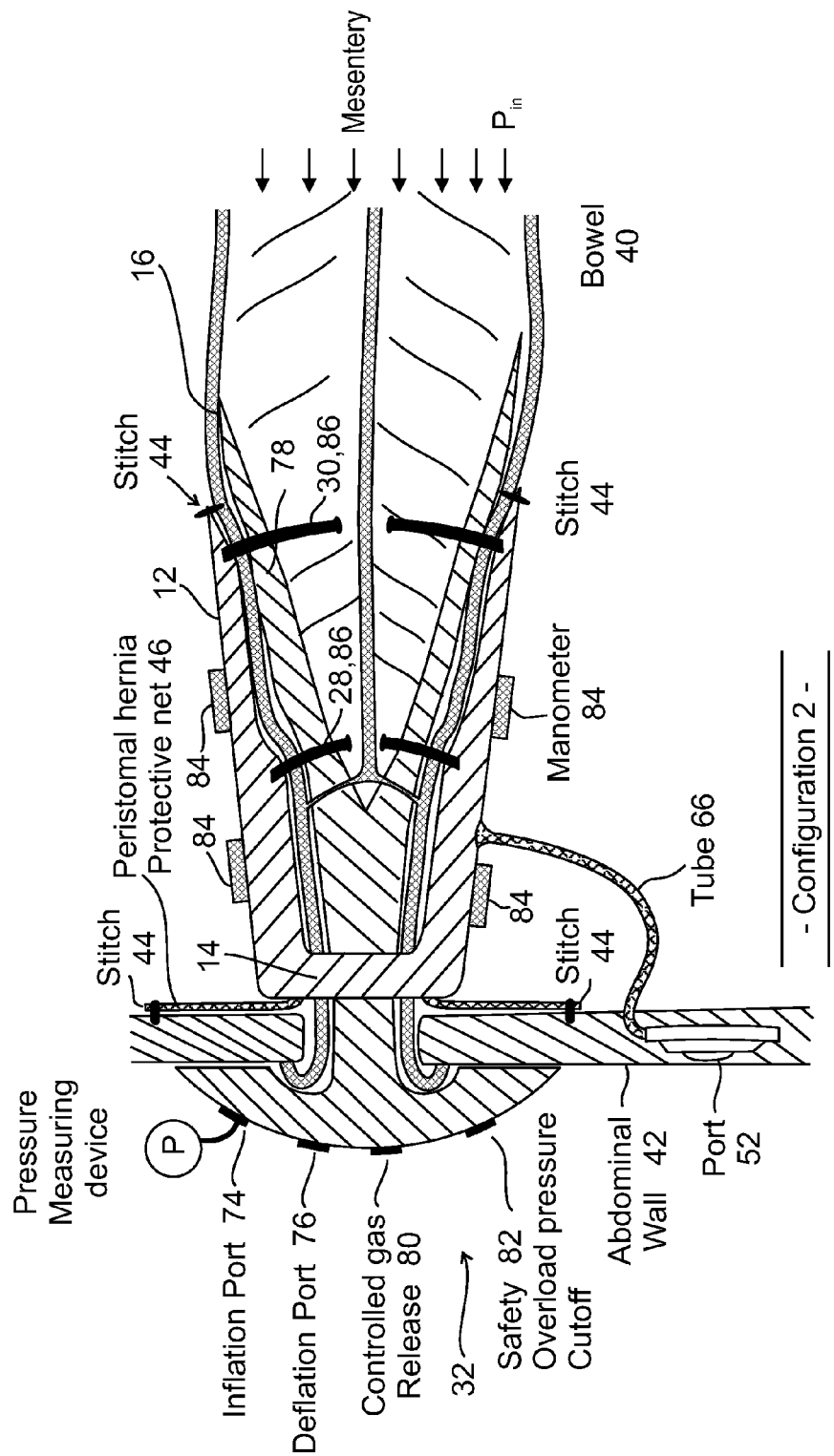
FIG. 11 shows an alternative embodiment of the implant of the present invention.

FIG. 11 shows an alternative embodiment of the implant of the present invention. Implant 10 comprises longitudinal section 12, having proximal end 14, and distal end 16. Longitudinal section 12 is positioned around at least a portion of bowel 40, and secured thereto and to abdominal wall 42 by stitches 44 and pins 86. Pressure-exerting device 78 comprises an inflatable-deflatable balloon, fixedly attached to distal end of removable closure 32. Removable closure 32 is positioned within proximal end 14 prior to inflation of pressure-exerting device 78. An outer surface of removable closure 32 is preferably provided with at least one of an inflation port 74; a deflation port 76; a valve 80 for controlled gas release, which may be controlled automatically, or manually by the user; and a safety cut off valve 82 which is automatically activated upon build up of pressure beyond a predetermined safety limit. The pressure level within implant 10 is monitored by manometer 84 located on longitudinal portion 12, and may be further connected to a warning device providing, for example, a visual or audible signal which alerts the user to evacuate the contents of the implant once a critical level is reached.

The implant, in the inflated mode, provides stomal continence, enabling the user to participate in normal social activities, including swimming.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A stomal implant comprising:
   a longitudinal portion configured to envelop at least a section of a bowel or ileal conduit, said longitudinal portion including:
      a proximal end for positioning at a stomal opening, and
      a distal end for positioning within an abdomen;
   a removable closure including a base located at a proximal end outside of said abdomen and a protruding section for insertion within said stomal opening; and
   a plurality of pressure-exerting devices, comprising a first pressure-exerting device fixedly attached to a distal end of said removable closure, and a second pressure-exerting device integral with said longitudinal portion;
   wherein upon insertion of said first pressure-exerting device attached to said removable closure within said proximal end of said longitudinal portion and activation of said first and second pressure-exerting devices, a pressure gradient is provided by pressing of said section of bowel or ileal conduit between said removable closure and said longitudinal portion along said section of the bowel or ileal conduit, said pressure gradient providing closure of said bowel or ileal conduit.

2. The stomal implant of claim 1 wherein said plurality of pressure-exerting devices comprises at least one inflatable device, said at least one inflatable device being inflated by insertion of a fluid.

3. The stomal implant of claim 2, wherein said fluid, prior to inflation of said at least one inflatable device of said second pressure-exerting device, is contained within a reservoir.

4. The stomal implant of claim 3, wherein said reservoir is located on an outer surface of said longitudinal portion.

5. The stomal implant of claim 3, wherein said at least one inflatable device of said second pressure-exerting device comprises a plurality of inflatable devices, and wherein said reservoir comprises a plurality of separate compartments, wherein each of said compartments serves as a reservoir for a corresponding subset of the plurality of inflatable devices, said subset being mutually distinct among said compartments.

6. The stomal implant of claim 3, further comprising an activator valve in communication with said reservoir, wherein activation of said activator valve forces said fluid from said reservoir into said at least one inflatable device of said second pressure-exerting device.

7. The stomal implant of claim 6, wherein said activator valve is positioned subcutaneously.

8. The stomal implant of claim 3, wherein said fluid is selected from the group consisting of a liquid, a gel, a colloid, a suspension, an emulsion, a gas, and a supercritical fluid.

9. The stomal implant of claim 8, wherein said liquid comprises saline.

10. The stomal implant of claim 3, further comprising a port, in fluid communication with said reservoir, wherein said port provides control of flow of said fluid from said reservoir to said at least one inflatable device of said second pressure-exerting device.

11. The stomal implant of claim 1, wherein said longitudinal portion is adapted to be attached to the intra-abdominal wall by at least one selected from the group consisting of a suture, a clip or a staple, or combinations thereof.

12. The stomal implant of claim 1, wherein the implant is constructed from silicon or polyurethane.

13. The stomal implant of claim 1, wherein said removable closure comprises a reversibly inflatable balloon the distal end of said removable closure.

14. The stomal implant of claim 1, further comprising a protective layer for positioning around said proximal end for prevention of peristomal hernia.

15. The stomal implant of claim 1, wherein said first pressure-exerting device comprises a reversibly inflatable balloon fixedly attached to the distal end of said removable closure.

16. The stomal implant of claim 1, wherein said removable closure further comprises at least one of a unidirectional gas valve, an inflation port, a deflation port and a pressure overload cutoff valve.

17. The stomal implant of claim 16, comprising said unidirectional gas valve, and wherein said unidirectional gas valve is disposed and configured to be manually controllable by a user while said removable closure is inserted.

18. The stomal implant of claim 17, comprising said pressure overload cutoff valve, and wherein said pressure overload cutoff valve is configured to release gas automatically above a predetermined safety limit threshold of pressure exerted from within said section of bowel or ileal conduit, said predetermined safety limit being at least 60 mmHg.

19. The stomal implant of claim 1, wherein said provided pressure gradient does not exceed 30-60 mmHg.

20. A method for providing fecal continence, the method comprising:
    providing an implanted stomal implant comprising a longitudinal portion configured to envelop at least a section of a bowel or ileal conduit, said longitudinal portion comprising:
        a proximal end positioned at a stomal opening,
        a distal end positioned within an abdomen, and
        a first pressure-exerting device; and said stomal implant further comprising:
        a removable closure for insertion within said stomal opening, and
        a second pressure-exerting device fixedly attached to a distal end of said removable closure;
    inserting said second pressure-exerting device attached to said removable closure within said proximal end of said longitudinal portion; and
    activating said first and second pressure-exerting devices, such that a pressure gradient is provided by pressing of said section of bowel or ileal conduit between said removable closure and said longitudinal portion which retains said removable closure within said proximal end and provides closure of said bowel or ileal conduit.

21. The method of claim 20, wherein said removable closure comprises a pressure overload cutoff valve, and said pressure overload cutoff valve releases gas automatically above a predetermined safety limit threshold of pressure exerted from within said section of bowel or ileal conduit, said predetermined safety limit being at least 60 mmHg.

* * * * *